United States Patent [19]

Ma

[11] 4,314,556

[45] Feb. 9, 1982

[54] EMERGENCY SYRINGE

[76] Inventor: Austin C. Ma, 23812 Helsinki St., Mission Viejo, Calif. 92691

[21] Appl. No.: 141,877

[22] Filed: Apr. 21, 1980

[51] Int. Cl.³ ............................................. A61M 5/00
[52] U.S. Cl. ........................ 128/218 DA; 128/218 D
[58] Field of Search ....... 128/218 R, 218 D, 218 DA, 128/218 M, 234, 272.1, 272.3, 215, 216

[56] References Cited

U.S. PATENT DOCUMENTS

| | | | |
|---|---|---|---|
| 1,728,259 | 9/1929 | Cressler | 128/218 D |
| 2,268,994 | 1/1942 | Smith | 128/218 D |
| 2,283,234 | 5/1942 | Smith | 128/218 D |
| 2,313,483 | 3/1943 | Smith | 128/218 D |
| 2,390,246 | 12/1945 | Folkman | 128/218 D |
| 2,392,196 | 1/1946 | Smith | 128/218 D |

Primary Examiner—John D. Yasko
Attorney, Agent, or Firm—Fischer, Tachner & Strauss

[57] ABSTRACT

A hypodermic syringe of the type having a containment chamber for a long term storage of a liquid drug contained therein. The chamber is preferably of a tubular glass construction which includes at one end a truncated conical forward portion having an exit path which is normally blocked by a rubber stopper while the liquid drug is in storage. The stopper lies inside the chamber and is held in fixed displaced relation to the needle of the syringe on an extension support comprising part of a nose piece of generally cylindrical shape that overlies the conical portion of the chamber in concentric slideable engagement therewith. A rear piece in concentric fixed engagement with the rear portion of the chamber retains a plunger at that end of the chamber whereby the liquid drug contained therein may be dispensed from the chamber after the fluid path is opened. The nose piece and the rear piece terminate at about the mid-section of the container in annular flanges displaced parallel to each other whereby compressive force applied to such flanges results in movement of the nose piece toward the rear of the syringe disengaging the stopper from the conical portion of the glass tube container thus opening a fluid path for dispensing the drug through the needle of the syringe. In a preferred embodiment overlapping snaps are provided to lock the two flanges in parallel engagement after the nose piece is pulled rearwardly to open the fluid path.

11 Claims, 9 Drawing Figures

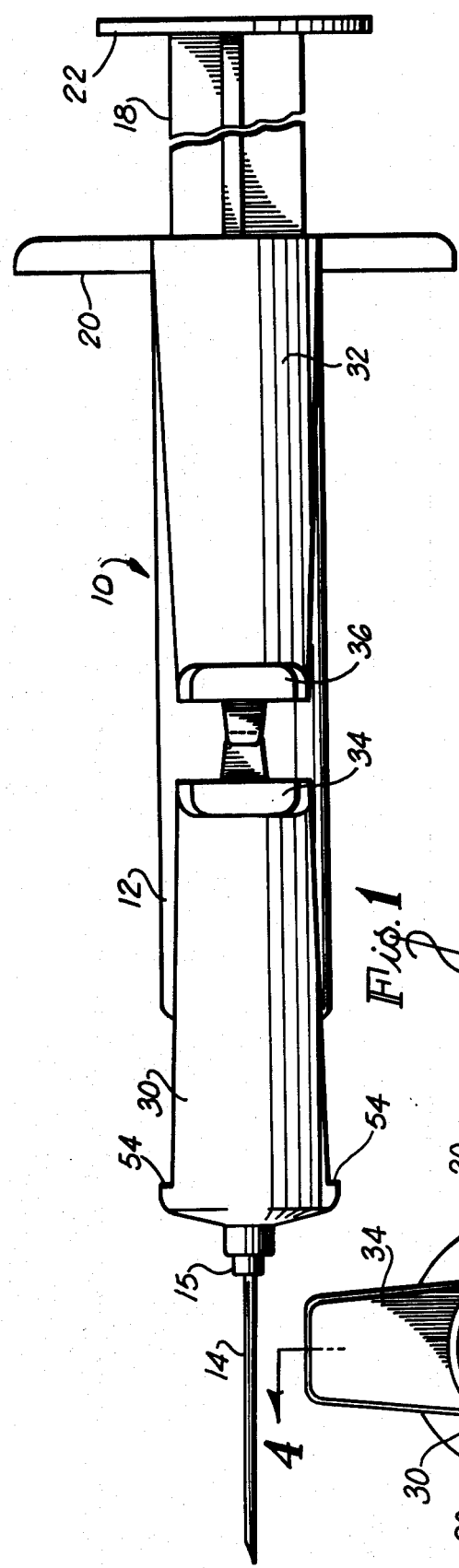
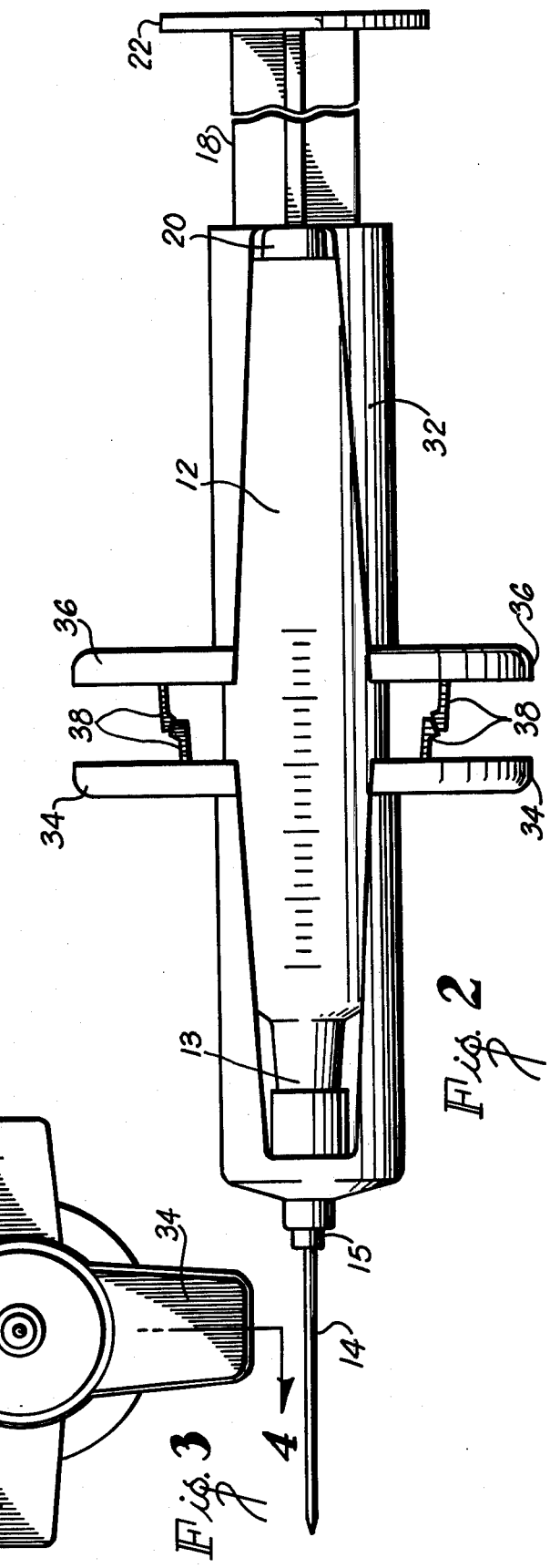

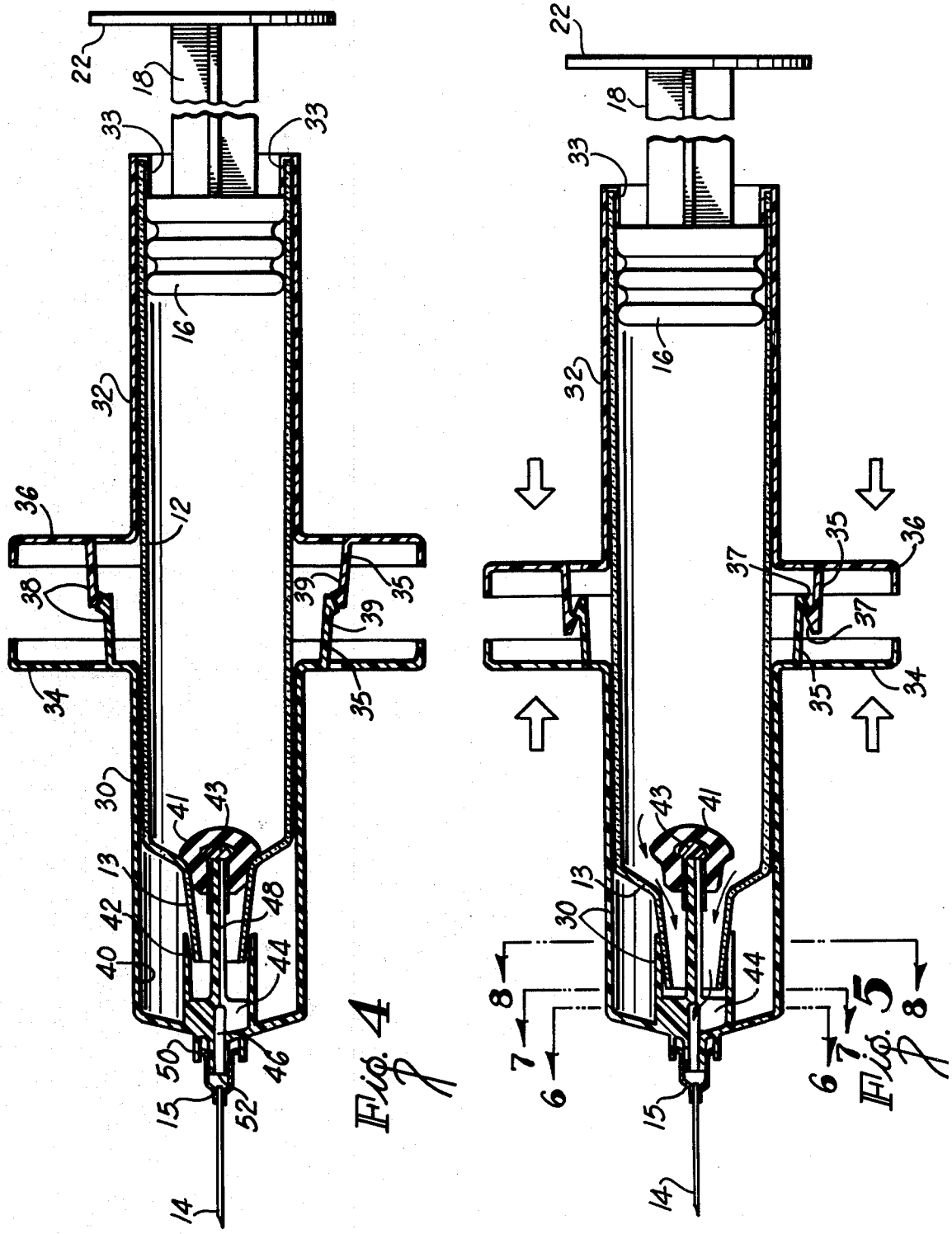

EMERGENCY SYRINGE

BACKGROUND OF THE INVENTION

1. Field of the Invention

This invention relates to hypodermic syringes for dispensing liquid drugs. More specifically, the present invention pertains to a syringe of the type having a prefilled containment chamber for long term storage of a drug in a known quantity in a sealed condition, and which is readily adapted for emergency dispensing of such stored liquid drug.

2. Prior Art

Numerous prior art emergency syringes are known. However, all such prior art emergency syringes known to the applicant suffer from a number of disadvantages which detrimentally affect their reliability and/or substantially increase their cost of manufacture. In addition, many such emergency syringes of the prior art function in a manner which is inherently dangerous to the patient by allowing the introduction of undesirable particulate matter into the drug as it is being dispensed or by allowing the introduction of a substantial amount of air into the patient along with the drug. In addition, many such prior art emergency syringes require the breaking of a seal or diaphragm which is uded to contain the drug in a non-contaminated condition in a storage chamber. Breaking or piercing such diaphragms requires a certain amount of force that varies significantly from syringe to syringe, rendering such prior art devices generally inconsistent and unpredictable in the degree of difficulty incurred to effect a configuration which permits dispensing of the drug into the patient.

By way of example, such prior art emergency syringes that utilize a diaphragm that is either burst or pierced immediately prior to, or concurrently with, the dispensing of the contained drug into the patient, are disclosed in many of the following patents.

| U.S. Pat. No. | U.S. Pat. No. |
|---|---|
| 2,362,165 | 3,391,695 |
| 2,538,390 | 3,413,974 |
| 2,538,391 | 3,424,155 |
| 2,646,798 | 3,710,794 |
| 2,735,429 | 3,739,779 |
| 2,778,360 | 3,757,779 |
| 2,841,144 | 3,757,780 |
| 3,091,240 | 3,768,473 |
| 3,308,821 | 3,803,700 |
| 3,380,449 | 3,859,999 |
| 3,387,609 | 3,885,297 |
| | 3,960,139 |

The devices disclosed in these patents are generally disadvantageous because the bursting or piercing of a diaphragm or similar structure tends to produce particulate matter that is carried by the drug into the patient and may thereby detrimentally affect the patient. In addition, the force needed to either pierce or burst a diaphragm or the like is generally not consistent from syringe to syringe because of the inherent difficulty in providing a diaphragm of precise dimensions. They must be sufficiently thick to provide adequate sealing and still be sufficiently thin to yield to a reasonable amount of piercing force. There is an additional problem incurred when emergency syringes utilizing diaphragms and the like contain drugs that are chemically active to result in increased pressure within the sealed containment chamber. By way of example, syringes of the type herein disclosed are desirable for emergency treatment of cardiac victims or the like wherein the drug contained in such syringes is sodium bicarbonate or the like. However, as is well known, most of such drugs are chemically active to the extent that some form of gaseous vapor such as carbon dioxide gas is given off, particularly at elevated temperatures. Accordingly, at higher temperatures, enough carbon dioxide gas may be produced to result in a pressure level within the containment chamber sufficient to prematurely burst or break the diaphragm and release the drug from the containment chamber, contaminating the drug and rendering the syringe useless.

Although one additional prior art emergency syringe known to the applicant does not fall within the above-indicated category of prior art syringes, it also suffers from a number of highly disadvantageous characteristics which render it far less desirable than the invention disclosed and claimed herein. More particularly, the device disclosed in U.S. Pat. No. 3,967,759 to Baldwin et al discloses a syringe that utilizes a pop-out valve plug seal in the nose end of a glass tube with a plunger piston at the opposite end.

Although the device disclosed by Baldwin et al (U.S. Pat. No. 3,967,759) is perhaps more relevant to the applicant's invention in that it does not require the use of a burstable or pierceable diaphragm, it still suffers from a number of disadvantages relating to the inconsistent amount of force required to unseal the containment chamber, the high cost of manufacture, and the potentially dangerous, unacceptably large volume of air that is introduced with the liquid drug dispensed into the patient, with or without an attempted purging of the air prior to injection. In addition, its structure still renders it susceptable to premature escape of the liquid drug within the containment chamber in applications involving sodium bicarbonate solution and similar drugs in which there is a substantial increase in internal vapor pressure, particularly at elevated temperatures. In addition, very precise manufacturing tolerances for an unusual glass tube geometry disclosed in the above-indicated Baldwin et al patent, increases the cost of manufacture. Further, during the drug dispensing (injection) process, the loosened rubber stopper may unexpectedly plug the fluid path and stop the dispensing which can be dangerous or even fatal to the patient.

SUMMARY OF THE INVENTION

The present invention overcomes or substantially reduces the noted disadvantages of the known prior art emergency syringes. The relative advantages of the present invention as compared to those devices disclosed in the above list of patents is relatively apparent in view of the implementation in the present invention of a containment chamber unsealing means which avoids use of diaphragms and the like and thus obviates bursting, breaking or sealing such diaphragms. The present invention is also advantageous as compared to the device disclosed in the Baldwin et al patent noted above. One such advantage is that the force applied to unseal the chamber in the present invention is not dependent upon force transmission from the piston at one end of the syringe through the contained liquid to the plug seal at the other end of the syringe as is the case in the Baldwin et al device. In addition, the unique structure of the present invention renders it relatively simple and easy to provide syringes with virtually identical force requirements to unseal the containment chamber and in which that force may be rendered of sufficiently low magnitude to enable personnel of even less than average strength to unseal the containment chamber at the time the syringe is to be used. In addition, and unlike the Baldwin et al syringe, the novel structure of the present invention provides a containment chamber which is far more resistant to increasing gas pressures and the like which would otherwise tend to prematurely unseal the chamber, contaminating the drug and rendering the device useless. In the present invention, as the internal pressure increases due to the evaporation or emission of gaseous vapor, the sealing effect of the stopper is increased due to the forward conical configuration of the invention as will be described below. Still another advantage over the Baldwin et al device is the relative simplicity of the structure of the glass tube container of the present invention which, contrary to the Baldwin et al syringe glass tube, is relatively inexpensive to manufacture and obviates presorting of the glass tubes during the process of assembling the syringe.

The present invention utilizes an elastic stopper, preferably made of rubber or similar material to seal the containment chamber. The containment chamber, which is preferably of a tubular glass construction, includes a truncated conical forward portion having an exit path which is normally blocked by the rubber stopper while the liquid drug is in storage. This conical forward portion of the glass tube is longitudinally displaced from the nose piece of the syringe. The nose piece is of generally cylindrical shape and includes structure at one end that is suitable for holding the syringe needle and for holding the rubber stopper in fixed, extended configuration relative to the needle. The nose piece is preferably made of a plastic material and includes a similarly configured conical portion which concentrically surrounds the conical portion of the glass tube in relatively slideable engagement. The advantageous conical matching between the plastic nose piece at the concentrically conical portion and the truncated conical forward portion of the glass tube allows a wide range of tolerances for both parts so that the cost of manufacturing both is substantially reduced. The plastic nose piece terminates at its other end at about the mid-section of the glass tube in an annular flange. A second plastic cylindrical container, in concentric fixed engagement with the rear portion of the glass tube container, is configured at one end in a wrap-around relation with the rear port of the container as will be more fully explained hereinafter. At its other end, the second plastic cylinder also terminates at the approximate mid-section of the glass container in a similar annular flange which is in displaced parallel relation to the annular flange of the nose piece. A plunger, inserted within the glass tube at the rear port thereof, includes a resilient portion of rubber material or the like which closes the rear end of the glass tube and which provides means for applying pressure to the liquid drug contained within the chamber after the fluid path is opened as will be explained hereinafter. The opening of the fluid path is accomplished by movement of the nose piece and stopper rearward with respect to the glass tube. This movement of the nose piece is accomplished by simply pulling the annular flange of the nose piece in a rearward direction toward the parallel annular flange of the second plastic cylinder, which pulling may be readily accomplished by holding the two flanges between the thumb and forefinger of one or both hands. In one embodiment of the present invention, overlapping snaps are provided to lock the two flanges in parallel engagement after the nose piece is pulled rearwardly to open the fluid path. Such locking prevents inadvertent disengagement of the plastic portions of the invention and ensures a continually opened fluid path.

OBJECTS OF THE INVENTION

It is therefore a principal object of the present invention to provide an emergency syringe which overcomes or substantially reduces the noted disadvantages of the prior art.

It is an additional object of the present invention to provide a syringe of the type including an openable sealed containment chamber for storing a liquid drug therein which precludes the use of diaphragms and the like, the opening of which would otherwise require bursting or piercing or the like.

It is still an additional object of the present invention to provide an emergency syringe of the type having a sealed containment chamber for storing a liquid drug therein in which the force required to unseal said chamber is generally consistent among a large plurality of such syringes.

It is still an additional object of the present invention to provide an emergency syringe of the type including a containment chamber for storing a liquid drug therein in which the process of unsealing said chamber introduces no substantial amount of particulate matter into said drug which would otherwise cause contamination.

It is still an additional object of the present invention to provide an emergency syringe of the type having a containment chamber for storing a liquid drug therein which chamber utilizes an openable sealing device which renders said chamber resistant to the buildup of vapor pressure within the chamber as a result of the chemical activity of the stored drug.

It is still an additional object of the present invention to provide an emergency syringe of the type having a containment chamber for storing a liquid drug therein in which said containment chamber comprises a simple cylindrical glass tube of simple low cost construction.

It is still an additional object of the present invention to provide an emergency syringe of the type having a containment chamber therein for storing a liquid drug, the chamber including a seal, the opening of which does not depend upon the transmission of force through the contained liquid to effect the opening of the fluid path for discharge of said drug.

It is still an additional object of the present invention to provide an emergency syringe of the type including a containment chamber for storing a liquid drug therein, which substantially reduces the volume of air between the containment chamber and the needle of the syringe as compared to the prior art.

BRIEF DESCRIPTION OF THE DRAWINGS

The above-indicated objects and advantages of the present invention, as well as additional objects and advantages, will be more fully understood by reference to the detailed description of a preferred embodiment taken in conjunction with the accompanying drawings in which:

FIG. 1 is a top exterior view of the present invention;

FIG. 2 is a front exterior view of the present invention;

FIG. 3 is an end exterior view of the present invention;

FIG. 4 is a sectional view of the present invention taken along lines 4—4 of FIG. 3 showing the invention in the storage configuration;

FIG. 5 is a sectional view of the present invention similar to FIG. 4 but showing the invention in the drug discharge configuration;

DETAILED DESCRIPTION OF A PREFERRED EMBODIMENT

Figure 6:
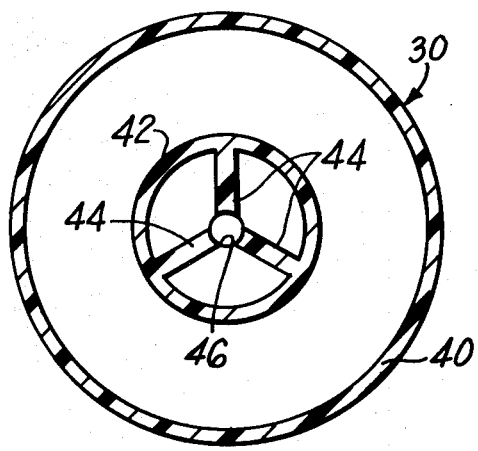
FIGS. 6 through 8 provide more detailed cross-sectional views of the fluid path portion of the present invention taken along lines 6—6, 7—7, and 8—8, respectively, of FIG. 5.

The general configuration of the present invention is evident in FIGS. 1 through 3. The invention, comprising the syringe 10, includes a containment chamber 12 in which a liquid drug to be dispensed by the present invention may be stored. As shown best in FIG. 1, containment chamber 12 comprises glass burette of generally tubular configuration which may include etched or printed volumetric lines to indicate the quantity of the liquid drug stored therein. Dispensing of the liquid drug stored within containment chamber 12 will be described hereinafter in more detail, but it is to be understood from FIGS. 1 through 5 that the liquid is dispensed through the conical portion 13 of containment chamber 12 and through needle 14 which is attached to the syringe by means of needle mounting hub 15 as seen best in FIGS. 1 and 2. The liquid drug may be dispensed after the containment chamber is unsealed as will be hereinafter more fully described. The dispensing results from the application of pressure to the plunger rod 18 which may preferably be accomplished by pulling on plunger grips 20 initially with the fingers while applying oppositely directed force from, for example, the palm of the same hand at the base of plunger flange 22 whereby the rod 18 is gradually inserted further into the containment chamber ejecting the fluid through needle 14. For purposes of description of the invention herein, the needle end of syringe 12 is referred to as the forward portion and the plunger end as the rear portion.

With the exception of conical portion 13 of containment chamber 12, the above indicated general features of the present invention are well known in the art and are not unique to the present invention. However, the structure of the present invention pertaining to the manner in which the containment chamber 12 is unsealed for the purpose of enabling the dispensing of the liquid drug contained therein and the structure pertaining to the manner in which the unsealed liquid flows from the containment chamber 12 in and through needle 14, is unique and will now be more fully described in conjunction with FIGS. 4 through 9.

As shown best in FIGS. 4 and 5, the front or forward portion of chamber 12, that is the portion closest to needle 14, lies within a generally cylindrical shaped nose piece 30 while the rearward portion of containment chamber 12, that is the portion closest to the plunger rod 18, lies within a generally cylindrical shaped rear piece 32. As shown further in FIGS. 4 and 5, rear piece 32 is, in effect, wrapped around the rear port of containment chamber 12 by means of plunger retainers 33 which prevent the rubber plunger portion 16 of plunger rod 18 from being pulled out in a rearward direction from the containment chamber.

Both nose piece 30 and rear piece 32 terminate at about the mid-section of containment chamber 12 in respective pairs of annular flanges 34 and 36. As will be more fully understood hereinafter, flanges 34 and 36 provide the means for pulling the nose piece rearward with respect to the containment chamber thus unsealing that chamber and providing a flowpath for the liquid drug contained therein. As shown in FIG. 4, which corresponds to the storage configuration of the present invention, annular flanges or front flanges 34 of nose piece 30 are substantially parallel to and spaced from corresponding rear flanges 36 of rear piece 32. Each such flange 34 and 36 includes a snap segment 38 which is substantially parallel to the longitudinal axis of the syringe. Each such snap segment 38 includes an extension 35 of substantially flat uniform rectangular cross-section which terminates in a trapezoidally shaped portion including snap stop surface 37 and snap retention surface 39. As shown in FIG. 4, the respective snap stop surfaces 37 are in frictional contact when flanges 34 and 36 are positioned farthest apart from one another whereby the surfaces 37 provide means for properly positioning nose piece 30 and rear piece 32 with respect to each other in the sealed configuration of the invention. However, after the containment chamber is unsealed as shown in FIG. 5, it is the snap retention surfaces 39 of the respective oppositely facing flanges 34 and 36 which are in contact to provide means for retaining the nose piece 30 and rear piece 32 in proper relation corresponding to the unsealed configuration of containment chamber 12.

As shown in FIGS. 4 and 5, the exterior forward portion of nose piece 30 includes a suitable outer annulus 50 and hub support 52 for threadably receiving the needle hub 15 in a conventional manner. The interior forward portion of nose piece 30 has, extending from outer surface 40, an inner annulus 42 concentrically positioned with respect to the longitudinal axis of syringe 10. Annulus 42 provides support for a tri-pillar structure 44 and stopper support 48 which provide a fluid flow path into the orifice 46 passing through the central front portion of nose piece 30 into the needle hub 15 and through the needle 14 through which the liquid drug flows when it is dispensed.

Stopper support 48 supports a stopper 41 preferably made of an elastic material such as rubber and the like which is chemically inert to the drug contained within chamber 12 and which is sufficiently elastic to provide a disengageable seal with respect to the conical tapered portion 13 of containment chamber 12. Stopper 41 overlies the rear end of support 48 in concentric engagement therewith. In the embodiment illustrated in FIGS. 4 and 5 an adapter 43 is utilized for the purpose of securing the attachment of stopper 41 on support 48. It will be understood however that the specific geometry of stopper 41 and support 48 may be modified to permit direct attachment of the stopper to the support without an adapter.

It will be seen that with stopper 41 mounted to the rear portion of support 48 in fixed spaced relation to needle 14, rearward motion of nose piece 30 relative to containment chamber 12, withdraws the stopper 41 from its sealed engagement within the tapered walls of conical portion 13 of the chamber thereby creating an annular flow path as shown in FIG. 5. Rearward motion of nose piece 30 for disengaging the stopper from conical portion 13 of containment chamber 12, is accomplished by pulling front flanges 34 of nose piece 30 rearwardly towards the corresponding rear flanges 36 of rear piece 32 as illustrated by the arrows in FIG. 5. Such rearward pulling may be accomplished by squeezing respective flanges 34 and 36 together on the respective sides of syringe 10, which may be easily accomplished by gripping the flanges between the thumb and forefinger of each hand and applying an adequate compressive force parallel to the longitudinal axis of the syringe.

It will be clear that rear piece 32 is fixed in position relative to containment chamber 12 as a result of the wrap-around configuration of plunger retainers 33. Therefore only the nose piece 30 will move relative to containment chamber 12 and the result of that motion is the withdrawal of the stopper from its sealing engagement with the conical portion 13 of the containment chamber and the opening of the fluid path to permit the dispensing of the liquid drug contained within chamber 12. It will also be clear that once the fluid path is opened, the liquid drug is readily forced out of the containment chamber and through orifice 46 into needle 14 by pressure applied through plunger 16, plunger rod 18 and flange 22 as the plunger is progressively forced in through containment chamber 12 towards the front portion thereof.

It will be observed that unlike the prior art emergency syringes previously discussed, in the present invention sealed containment chamber 12 is unsealed without requiring any type of bursting or piercing of a diaphragm and also without requiring the application of a force through the liquid drug. In the present invention, a force is not applied through the plunger until after the fluid path is opened by the relative movement of the flanges 34 and 36 as described above. It should also be observed that the inner surface of inner annulus 42 adjacent conical portion 13 is tapered so that relative motion between the forward-most structure of conical portion 13 of chamber 12 and nose piece 30 may take place despite variations in the precise geometry of the conical portion. The relative motion between the conical portion 13 and nose piece 30 is observed by comparing their relative positions as shown in the sealed configuration of FIG. 4 and the opened fluid path configuration of FIG. 5.

Figure 7:
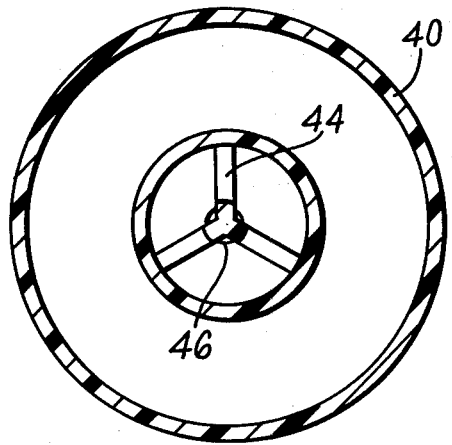
Figure 8:
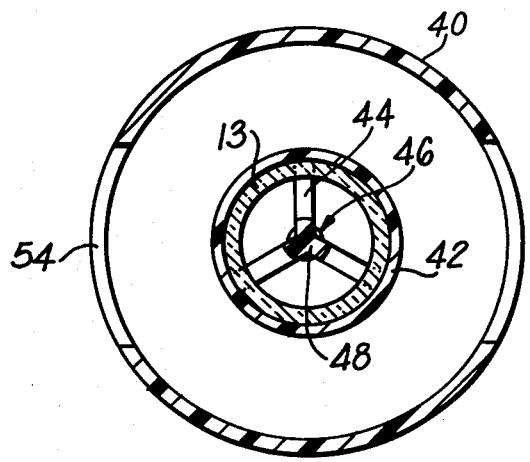
Figure 9:
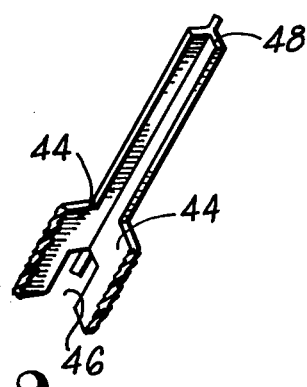
FIG. 9 is a three-dimensional view of the flow path portion of the present invention.

The sectional views comprising FIGS. 6, 7, and 8 illustrate the detailed structure of the forward portion of nose piece 30 including that portion of the fluid flow path through which the liquid drug is dispensed from the containment chamber 12 into the needle 14 after nose piece 30 is pulled back, thereby disengaging stopper 41 from conical portion 13 of the chamber. It is to be noted that nose piece 30 is, in the preferred embodiment of the present invention, a unitary injection molded structure of a substantially transparent plastic material such as polypropylene. Accordingly, it will be observed that FIG. 9, which provides a three dimensional view of the portion of the nose piece 30 comprising pillars 44 and stopper support 48, is included to more fully illustrate the manner in which fluid passes into orifice 46 and through needle 14, but it is not meant to indicate that nose piece 30 need comprise separate detachable elements.

As shown in FIGS. 6 through 9, the forward portion of nose piece 30 comprises an outer surface 40 of circular cylindrical shape and a concentrically located inner annulus 42 which is divided equiangularly by three pillars 44. At the location corresponding to the section seen in FIG. 6, the intersection of the three pillars along the longitudinal axis of the syringe is cut away to provide a diameter substantially equal to that of orifice 46. However at the location corresponding to FIG. 7, the three pillars 44 extend completely into the center of inner annulus 42 to meet at a line corresponding to the axis of the syringe. The orifice 46 can be seen partially in FIG. 7. In FIG. 8, the sectional view corresponds to a location rearward of the end of annulus 42 intersecting stopper support 48. The section corresponding to FIG. 8 is sufficiently rearward of the forward-most portion of nose piece 30 so that it is now possible to see the window perimeter of nose piece 30 as non-sectioned surfaces 54 which are also seen in FIGS. 1 and 2.

It will now be observed that because of the constriction of the conical portion 13 of the containment chamber 12 that is forward of stopper 41, and as a result of the limited amount of non-occupied space within the annulus 42 along the flow path of the liquid drug to be dispensed, the present invention provides the added advantage of substantially reducing the volume of air that is likely to be dispensed with the liquid drug into a patient during emergency utilization of the syringe of the present invention. Thus, in those circumstances where it is undesirable or inconvenient to first insert the plunger partially to force air out through the needle before the liquid drug is dispensed into the patient, only a relatively small volume of air is injected into the patient along with the liquid drug. Even when purging is accomplished before injecting the needle into the patient, the present invention is superior because it does away with complex geometrical regions where trapped gases could otherwise resist purging.

It will now also be observed that in the present invention the unique sealing structure renders it possible to reseal the containment chamber after a portion of the drug has been dispensed into the patient. Resealing may be readily accomplished by first maneuvering snaps 38 to disengage the retention surfaces 39 and then by pulling the nose piece 30 forward to reinsert stopper 41 into the neck down portion of the containment chamber. Although the need for resealing an emergency syringe may be of only occasional value, resealing is simply not possible in all the previously described prior art in which unsealing depends upon either the piercing, breaking, or bursting of a diaphragm or the use of a pop-out device which depends upon the application of force by the plunger, through the liquid drug, to unseal the chamber.

It will now be understood that what has been disclosed herein is a unique emergency syringe that utilizes a stopper of elastic material to seal a containment chamber for storing a liquid drug. The chamber is preferably made of tubular glass construction and the stopper is inserted in sealing engagement with the walls of a truncated conical forward portion of the chamber in longitudinally displaced position relative to the needle of the syringe. A nose piece and rear piece of generally cylindrical configuration concentrically surround the forward and rear portion, respectively, of the glass tube. The nose piece is configured in relative slideable engagement with the glass tube so that when it is forced rearwardly, the nose piece forces the stopper away from the truncated conical portion of the containment chamber opening a fluid path through which the liquid drug may be forced by a plunger at the rearward port of the containment chamber.

It will now also be understood that what has been disclosed herein is a unique emergency syringe which does not require the use of a diaphragm that must otherwise be burst or pierced to provide a fluid path to dispense the liquid drug contained therein. It will now be understood that no particulate matter is introduced into the drug as a result of unsealing the containment chamber of the present invention. In addition, because the unique structure of the present invention includes a chamber stopper configuration in which the stopper is forced further into the containment chamber to open a fluid path, the chamber of the present invention is resistant to increased vapor pressure within the chamber which may result from the chemical activity of the stored drug particularly at elevated temperatures. It will be observed that the containment chamber of the present invention utilizes a relatively simple cylindrical glass tube of low cost construction and that the means for unsealing the chamber of the present invention does not depend upon the transmission of force through the contained liquid but instead utilizes a force applied to external concentric plastic flanges to force the stopper toward the interior of the chamber whereby the force to unseal the chamber is generally consistent among a large plurality of syringes. Finally, it will now be understood that the present invention utilizes a novel structure which allows a substantial reduction in the volume of air between the containment chamber and the needle of the syringe as compared to prior art emergency syringes.

Although a preferred embodiment of the best mode of the invention has been disclosed in sufficient detail to enable one skilled in the art to make and use the invention, it will now be understood that various modifications may be made to the specific geometry, dimensions, and materials disclosed herein but that all such modifications are contemplated to be within the scope of the invention which is to be limited only by the appended claims.

I claim:

1. In a hypodermic syringe of the type having a containment chamber for long term sealed storage of a liquid therein and having means for dispensing the stored liquid through a channeled needle after the containment chamber is unsealed, the combination comprising:
   a constricted opening in said chamber forming a fluid path therein, said fluid path being in substantial proximity to said dispensing means,
   a stopper inside said chamber in blocking engagement with said fluid path,
   means for pushing said stopper further into said chamber without increasing the pressure in said chamber and for holding said stopper in fixed displacement from said fluid path thereby unsealing said chamber, and
   means for forcing said liquid through said fluid path and in to said dispensing means.

2. The combination defined in claim 1 wherein which said containment chamber comprises a tubular glass burette and wherein said constriction comprises a truncated conical forward portion of said burette.

3. The combination defined in claim 2 wherein said pushing means comprises a nose piece of substantially cylindrical cross-section overlying said constriction of said burette in relative slidable engagement therewith and having a centrally located extention support for holding said stopper whereby rearward movement of said nose piece relative to said burette unseals said chamber.

4. The combination recited in claim 3 further comprising a rear piece of substantially cylindrical cross-section overlying the rearward portion of said burette in substantially fixed concentric engagement therewith.

5. The combination recited in claim 4 further comprising annular flanges at least one of which is located on said nose piece and at least one of which is located in opposing parallel ralation thereto on said rear piece whereby the application of a compressive force between said flanges results in motion of said nose piece towards said rear piece thereby unsealing said chamber.

6. The combination recited in claim 5 further comprising means for retaining said flanges in fixed parallel displacement relative to one another when said chamber is sealed and means for retaining said flanges in fixed parallel displacement when said chamber is unsealed.

7. The combination recited in claim 4 further comprising means on said rear piece folded into a nonconstricted second opening in said chamber for retaining said forcing means in said chamber.

8. An emergency hypodermic syringe comprising:
   a substantially tubular burette having openings at the respective longitudinal ends thereof, one such opening being substantially smaller in diameter than the nominal diameter of the burette, said smaller opening being formed at the terminus of a truncated substantially conical portion of said burette,
   a stopper of substantially elastic material positioned within said burette in substantial proximity to said conical portion and of substantially conical cross-section of sufficient dimension to block said smaller opening when in compressive concentric engagement with said conical portion,
   a channeled needle for injecting said syringe and for dispensing a liquid therethrough,
   a nose piece of substantially cylindrical cross-section overlying said conical portion of said burette in relative slideable engagement therewith and having means for holding said stopper and said needle in fixed relative displacement whereby motion of said noise piece towards said burette disengages said stopper from said conical portion, and
   a plunger enclosing the other opening of said burette for forcing said liquid out of said burette after said stopper is disengaged from said conical portion.

9. An emergency hypodermic syringe as defined in claim 8 further comprising:
   a rear piece of substantially cylindrical cross-section overlying the rear-most portion of said burette in concentric fixed engagement therewith.

10. An emergency hypodermic syringe as defined in claim 9 further comprising at least one flange on each of said nose piece and rear piece, said flanges being in displaced parallel position relative to one another whereby a compressive force applied therebetween results in motion of said nose piece towards said burette for disengaging said stopper from said conical portion.

11. An emergency hypodermic syringe as defined in claim 10 further comprising means for securing said flanges in fixed relative displacement to each other after said stopper is disengaged from said conical portion.

* * * * *